US00PP19338P3

(12) United States Plant Patent
Layt

(10) Patent No.: US PP19,338 P3
(45) Date of Patent: Oct. 14, 2008

(54) ***DIANELLA* PLANT NAMED 'TAS100'**

(50) Latin Name: *Dianella tasmanica*
Varietal Denomination: TAS100

(75) Inventor: Todd Anthony Layt, Clarendon (AU)

(73) Assignee: Ozbreed Pty. Ltd. of Richmond, New South Wales (AU)

( * ) Notice: Subject to any disclaimer, the term of this patent is extended or adjusted under 35 U.S.C. 154(b) by 0 days.

(21) Appl. No.: 11/657,361

(22) Filed: Jan. 24, 2007

(65) Prior Publication Data

US 2008/0184445 P1 Jul. 31, 2008

(51) Int. Cl.
*A01H 5/00* (2006.01)

(52) U.S. Cl. ..... Plt./424

(58) Field of Classification Search ..... Plt./424, Plt./263, 263.1

See application file for complete search history.

*Primary Examiner*—Annette H Para
(74) *Attorney, Agent, or Firm*—C. A. Whealy

(57) ABSTRACT

A new and distinct cultivar of *Dianella* plant named 'TAS100', characterized by its compact, upright and outwardly arching plant habit; moderately dense growth habit; numerous linear leaves arranged in a basal rosette; variegated green and creamy white-colored leaves; and good garden performance.

1 Drawing Sheet

Botanical designation: *Dianella tasmanica.*
Cultivar denomination: 'TAS100'.

BACKGROUND OF THE INVENTION

The present invention relates to a new and distinct cultivar of *Dianella* plant, botanically known as *Dianella tasmanica,* and hereinafter referred to by the name 'TAS100'.

The new *Dianella* is a naturally-occurring whole plant mutation of an unnamed selection of *Dianella tasmanica,* not patented. The new *Dianella* was discovered and selected by the Inventor as a single plant from within a population of plants of the parent selection in a controlled environment in Sydney, New South Wales, Australia in January, 2005.

Asexual reproduction of the new *Dianella* by micropropagation in Sydney, New South Wales, Australia since February, 2005, has shown that the unique features of this new *Dianella* are stable and reproduced true to type in successive generations.

SUMMARY OF THE INVENTION

The cultivar TAS100 has not been observed under all possible environmental conditions. The phenotype may vary somewhat with variations in environment such as temperature and light intensity, without, however, any variance in genotype.

The following traits have been repeatedly observed and are determined to be the unique characteristics of 'TAS100'. These characteristics in combination distinguish 'TAS100' as a new and distinct cultivar of *Dianella:*

1. Compact, upright and outwardly arching plant habit.
2. Moderately dense growth habit.
3. Numerous linear leaves arranged in a basal rosette.
4. Variegated green and creamy white-colored leaves.
5. Good garden performance.

In side-by-side comparisons conducted in Sydney, New South Wales, Australia, plants of the new *Dianella* differed from plants of the parent selection in the following characteristics:

1. Plants of the new *Dianella* were more compact than plants of the parent selection.
2. Plants of the new *Dianella* were more dense than plants of the parent selection.
3. Leaves of plants of the new *Dianella* had broader creamy white-colored longitudinal stripes than leaves of plants of the parent selection.

Plants of the new *Dianella* can be compared to plants of the *Dianella* cultivar Sougold, disclosed in U.S. Plant Pat. No. 13,705. Plants of the new *Dianella* differ primarily from plants of the cultivar Sougold in foliage coloration as plants of the cultivar Sougold have green and gold-colored variegated foliage.

Plants of the new *Dianella* can be compared to plants of the *Dianella* cultivar Splice, not patented. Plants of the new *Dianella* differ primarily from plants of the cultivar Splice in foliage coloration as plants of the cultivar Splice have green and yellow-colored variegated foliage.

BRIEF DESCRIPTION OF THE PHOTOGRAPH

The accompanying photograph illustrates the overall appearance of the new *Dianella.* This photograph shows the colors as true as it is reasonably possible to obtain in colored reproductions of this type. Colors in the photograph may differ slightly from the color values cited in the detailed botanical description which accurately describe the colors of the new *Dianella.* The photograph comprises a side perspective view of a typical ten-month old plant of 'TAS100' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Sydney, New South Wales, Australia during the summer in an outdoor nursery and under conditions and practices which approximate those generally used in commercial *Dianella* production. Measurements and numerical values represent averages for typical ten-month old plants grown in containers and in ground beds.

Botanical classification: *Dianella tasmanica* cultivar TAS100.

Parentage: Naturally-occurring whole plant mutation of an unnamed selection of *Dianella tasmanica,* not patented.

Propagation:

*Type.*—By micropropagation.

*Root description.*—Fibrous.

Plant description:

*Plant form/growth habit.*—Compact, upright and outwardly arching plant habit; moderately dense growth habit.

*Plant height.*—About 40 cm.

*Plant diameter or spread.*—About 40 cm.

Foliage description:

*Arrangement.*—Two-ranked, simple.

*Length.*—About 40 cm.

*Width.*—About 5 cm.

*Shape.*—Linear.

*Apex.*—Tapering to a point.

*Margin.*—Entire.

*Aspect.*—Initially upright then outwardly arching with development.

*Texture, upper and lower surfaces.*—Smooth, glabrous.

*Venation pattern.*—Parallel.

*Color.*—Developing and fully expanded foliage, upper surface: Green ground color, close to 147B; parallel creamy white longitudinal stripes, ranging from close to 11D to close to 158D; stripes irregular in width. Developing and fully expanded foliage, lower surface: Green ground color, close to 147B; parallel creamy white longitudinal stripes, ranging from close to 11D to close to 158D; stripes irregular in width. Venation, upper and lower surfaces: Similar to lamina coloration.

Flower description: Inflorescence and flower development has not been observed on plants of the new *Dianella.* Plants of the new *Dianella* do not develop flowers.

Disease/pest resistance: Plants of the new *Dianella* have not been shown to be resistant to pathogens and pests common to *Dianella.*

Garden performance: Plants of the new *Dianella* have been observed to have good garden performance and tolerate wind, rain and temperatures ranging from about −10° C. to about 43° C.

It is claimed:

1. A new and distinct *Dianella* plant named 'TAS100' as illustrated and described.

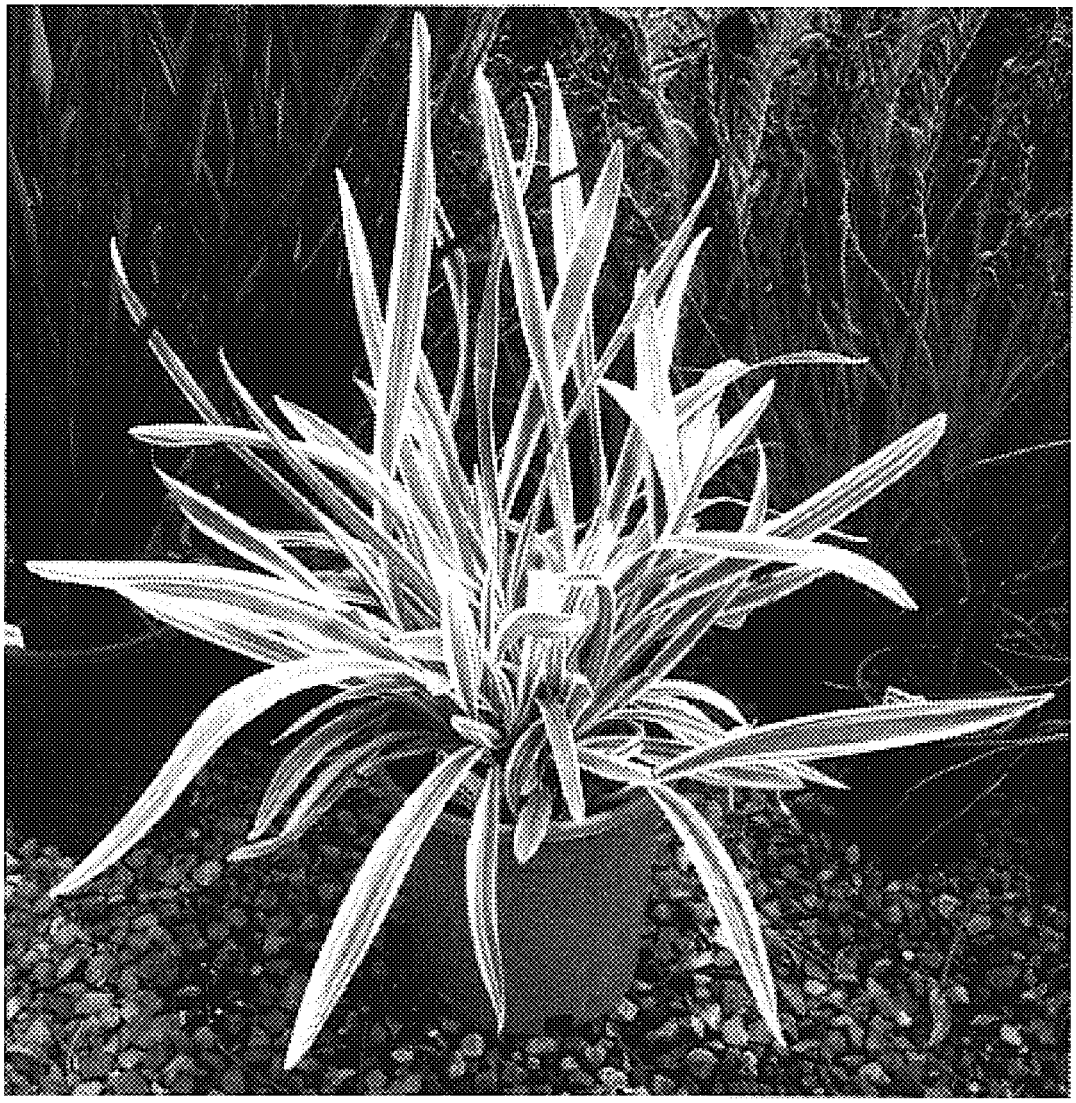

* * * * *